(12) United States Patent
Camus

(10) Patent No.: US 7,857,512 B2
(45) Date of Patent: Dec. 28, 2010

(54) COLLISION PROTECTION DEVICE FOR A PATIENT EXAMINATION TABLE OF A MEDICAL X-RAY DEVICE

(75) Inventor: Estelle Camus, Mountain View, CA (US)

(73) Assignee: Siemens Aktiengesellschaft, Munich (DE)

( * ) Notice: Subject to any disclaimer, the term of this patent is extended or adjusted under 35 U.S.C. 154(b) by 26 days.

(21) Appl. No.: 12/156,592

(22) Filed: Jun. 2, 2008

(65) Prior Publication Data

US 2008/0304626 A1 Dec. 11, 2008

(30) Foreign Application Priority Data

Jun. 4, 2007 (DE) .................. 10 2007 025 935

(51) Int. Cl.
*H05G 1/02* (2006.01)
*A61B 6/04* (2006.01)

(52) U.S. Cl. ............. 378/196; 378/197; 378/204; 378/209; 5/424; 5/601

(58) Field of Classification Search ........... 378/203, 378/204, 209, 196, 197; 5/424, 601
See application file for complete search history.

(56) References Cited

U.S. PATENT DOCUMENTS

| | | | | |
|---|---|---|---|---|
| 4,193,148 A | * | 3/1980 | Rush | 378/177 |
| 5,651,044 A | * | 7/1997 | Klotz et al. | 378/117 |
| 5,654,997 A | * | 8/1997 | Brownell et al. | 378/117 |
| 5,805,664 A | * | 9/1998 | Whipple et al. | 378/117 |
| 5,883,935 A | * | 3/1999 | Habraken et al. | 378/117 |
| 5,892,238 A | | 4/1999 | Huttner et al. | |
| 5,928,149 A | * | 7/1999 | Habraken | 600/425 |
| 6,408,051 B2 | * | 6/2002 | Habraken et al. | 378/117 |
| 6,456,684 B1 | * | 9/2002 | Mun et al. | 378/20 |
| 6,722,783 B2 | * | 4/2004 | Jackson, Sr. | 378/178 |
| 6,869,217 B2 | * | 3/2005 | Rasche et al. | 378/197 |
| 6,955,464 B1 | * | 10/2005 | Tybinkowski et al. | 378/209 |
| 6,985,556 B2 | * | 1/2006 | Shanmugavel et al. | 378/117 |
| 6,988,284 B2 | * | 1/2006 | Bannister | 5/601 |
| 7,172,340 B2 | * | 2/2007 | Oota | 378/189 |
| 7,489,142 B2 | * | 2/2009 | Somers | 324/661 |
| 7,492,858 B2 | * | 2/2009 | Partain et al. | 378/37 |
| 7,500,784 B2 | * | 3/2009 | Grebner et al. | 378/198 |
| 7,548,075 B2 | * | 6/2009 | Somers | 324/688 |
| 7,552,490 B2 | * | 6/2009 | Saracen et al. | 5/601 |
| 7,570,064 B2 | * | 8/2009 | Roziere | 324/662 |
| 7,638,784 B2 | * | 12/2009 | Fox et al. | 250/515.1 |
| 7,640,607 B2 | * | 1/2010 | Guertin et al. | 5/601 |

FOREIGN PATENT DOCUMENTS

DE   10 2006 007 833 A1   8/2006

* cited by examiner

*Primary Examiner*—Allen C. Ho

(57) ABSTRACT

The invention can be summarized as follows: A collision protection device for a patient examination table of a medical X-ray device is provided for the purpose of assuring simple and reliable avoidance of collisions between very fast moving device parts of a medical X-ray device and a patient, which collision protection device has a protective element made of an X-ray transparent material, wherein the collision protection device can be arranged relative to the patient examination table and brought into a position such that in said position the protective element mechanically shields at least a part of the lying surface of the patient examination table.

14 Claims, 2 Drawing Sheets

COLLISION PROTECTION DEVICE FOR A PATIENT EXAMINATION TABLE OF A MEDICAL X-RAY DEVICE

CROSS REFERENCE TO RELATED APPLICATIONS

This application claims priority of German application No. 10 2007 025 935.4 filed Jun. 4, 2007, which is incorporated by reference herein in its entirety.

FIELD OF THE INVENTION

The invention relates to a collision protection device for a patient examination table of a medical X-ray device and to a patient examination table having a collision protection device as well as to an X-ray device.

BACKGROUND OF THE INVENTION

In medical radiology, 3D images of a body are reconstructed with the aid of a C-arm rotating around a patient. In such an arrangement, images of high-contrast objects such as e.g. contrast-agent-filled vessels and images of low-contrast objects such as tissue are generated and 3-D structures can be visualized morphologically for interventional purposes. The rotations of the C-arm around a patient generally last about 5 seconds to 20 seconds. In order to obtain functional information in addition to the morphological data, a faster rotation of the C-arm around the patient is necessary.

The movement of the C-arm around the patient entails the risk of a collision of the C-arm, in particular of the X-ray detector or of the collimator, with the patient, staff or other objects of equipment in the room. This is usually avoided in current practice by the physician's performing a slow rotation monitored by him/her—a test run—before the automatic rotation is initiated. In this case he/she monitors the run for potential collisions. The most critical area is, of course, the area of the patient, especially in the event of unexpected patient movements.

In order to avoid injury to the patient as a result of a collision with the C-arm, additional sensors are mounted on the X-ray detector and the collimator. If said sensors are activated, the movement of the C-arm is stopped. If the rotation times are shortened, i.e. the rotation speeds are increased, this protection is no longer sufficient.

Solutions for collision avoidance have already been proposed, e.g. image-based monitoring approaches or approaches using a special collision sensor system (e.g. the non-pre-published patent application DE 10 2007 003 876.5).

SUMMARY OF THE INVENTION

It is the object of the present invention to provide a simple, robust device by means of which collisions, in particular of a rotating C-arm, in particular with a patient, are effectively avoided even at high rotation speeds.

The object is achieved according to the invention by a collision protection device for a patient examination table of a medical X-ray device and by a patient examination table having a collision protection device as well as by an X-ray device as claimed in the independent claims. Advantageous embodiments of the invention are the subject matter of the respective associated dependent claims.

It is proposed according to the invention to install a collision protection device having at least one protective element around the patient table, which protective element prevents a collision of an object in the direct patient environment, in particular the patient, with a moving device part, in particular a robot-controlled C-arm.

By means of the collision protection device according to the invention the patient on the patient examination table is mechanically shielded, at least partially, by means of one or more protective elements and in this way protected against a collision with a moving device part such as a moving C-arm. In this case the collision protection device according to the invention can be installed easily and quickly and with little effort and furthermore robustly and reliably. Systematic monitoring or a complex system of sensors can be dispensed with. In addition, the collision protection device according to the invention is not dependent on the rotational speed of the C-arm.

According to the invention the protective element or elements is or are embodied as X-ray transparent, with the result that no influencing of the quality of the recorded X-ray images occurs.

According to one embodiment of the invention, the collision protection device can be coupled to the patient examination table, in particular by means of at least one securing element. The collision protection device can be mounted on the patient examination table for example by means of fixing posts, in particular also in such a way that they can be removed again with a few hand movements. It can also be provided that the protective element is connected to the patient examination table in such a way that it can be moved into a shielding position and a parking position. This can be realized for example in that the protective element is disposed above the patient in the manner of a cover in the shielding position and is moved by folding into the parking position.

According to a further embodiment of the invention, the collision protection device has a stand or base by means of which it can be set up on the floor. In this way it can also be positioned in a manner that is decoupled from the patient examination table, for example by being pushed against the patient examination table and pushed away again after use.

The collision protection device advantageously has a drive by means of which the protective element can be brought into the corresponding position. This can be implemented both for the collision protection device coupled to the patient examination table and for the decoupled collision protection device.

According to further embodiments of the invention, the protective element has the form of a longitudinally sectioned cylinder or an elliptical paraboloid surface or a half-ellipsoid surface or a half-spherical surface or is cylindrical in shape. These shapes are particularly well suited as shields because they are cover- or hood-like and create a protected space around the patient.

The protective element is beneficially embodied as transparent. The protective element is advantageously embodied from plastic, in particular from a hard plastic. In order to minimize damage to the C-arm or X-ray detector in the event of a collision with the protective element, the protective element is coated on its outer surface with a flexible material, in particular a foam material.

According to a further embodiment of the invention, the collision protection device has at least one collision sensor. This is disposed in particular on the protective element. In this connection the collision protection device beneficially has a signal output device which, when the C-arm approaches for example, outputs an optical or acoustic warning signal or passes on such a signal to the X-ray device so that the movement can be stopped.

The invention also comprises a patient examination table having an inventive collision protection device which is structurally connected to the patient examination table, as well as an X-ray device having an X-ray emitter, an X-ray detector and a patient examination table, wherein the X-ray emitter and/or X-ray detector are carried on at least one movable robotic arm and wherein the collision protection device is provided to act as a mechanical shield against the movable robotic arm. According to a further embodiment of the invention, the robotic arm carries a C-arm and the X-ray emitter and X-ray detector are in each case disposed at opposite ends of the C-arm.

BRIEF DESCRIPTION OF THE DRAWINGS

The invention and further advantageous embodiments according to features of the dependent claims are explained in more detail below with reference to exemplary embodiments represented schematically in the drawing, without thereby restricting the invention to these exemplary embodiments; the figures show:

DETAILED DESCRIPTION OF THE INVENTION

Figure 1:
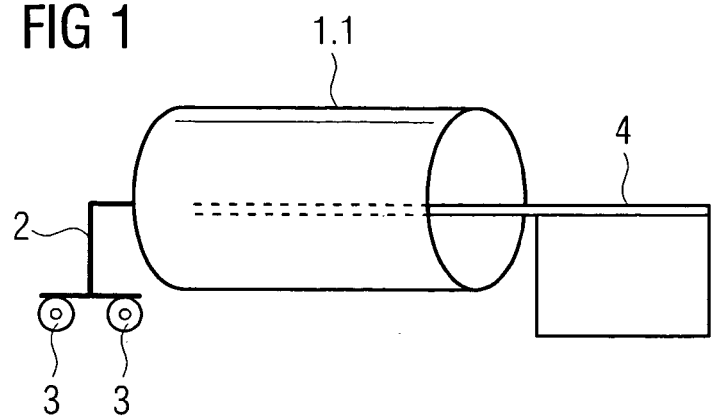
FIG. 1 a side view of an inventive collision protection device having a cylindrical protective element in a shielding position relative to a patient examination table.

FIG. 1 shows an inventive collision protection device having a cylindrical protective element 1.1 in a shielding position relative to a patient examination table 4. In this arrangement the cylindrical protective element 1.1 is disposed in such a way that at least a part of the patient examination table 4 and a patient lying thereon are enclosed by the cylindrical protective element 1.1. The cylindrical protective element 1.1 has a stand 2 with rollers 3 so that when necessary it can be moved into the shielding position around the patient examination table 4 and also be easily removed again.

Figure 2:
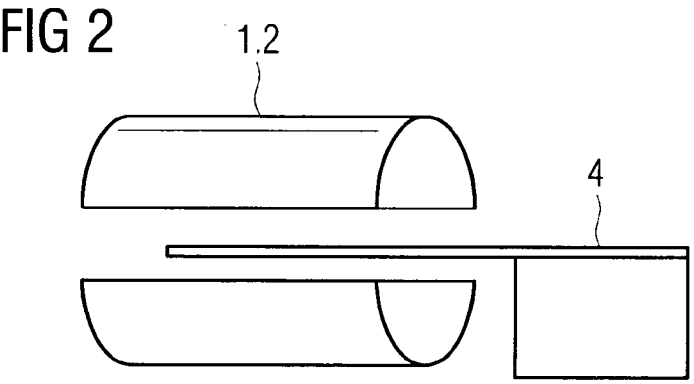
FIG. 2 a side view of an inventive collision protection device having two semi-cylindrical protective elements in a shielding position relative to a patient examination table.
Figure 4:
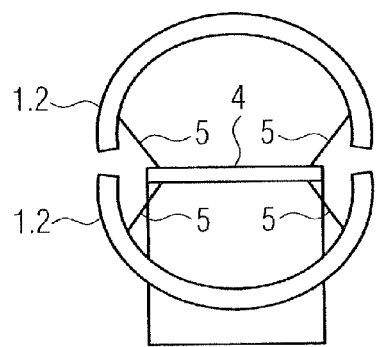
FIG. 4 a plan view onto a collision protection device according to FIG. 2 with securing elements for fixing to the patient examination table.

FIG. 2 shows a further inventive collision protection device having two semi-cylindrical protective elements 1.2 in a shielding position relative to a patient examination table 4, in this case disposed above and below the patient examination table 4. It is also possible for only one semi-cylindrical protective element 1.2 to be disposed above the patient examination table. The protective element can, for example, be secured—as shown in FIG. 4—to the patient examination table in a demountable manner by means of fixing posts 5. Patient examination table 4 and protective element 1.2 can also form a structural entity, the protective element then being foldable into a shielding position by means of a hinge and, when it is not needed, into a folded-away parking position.

Figure 3:
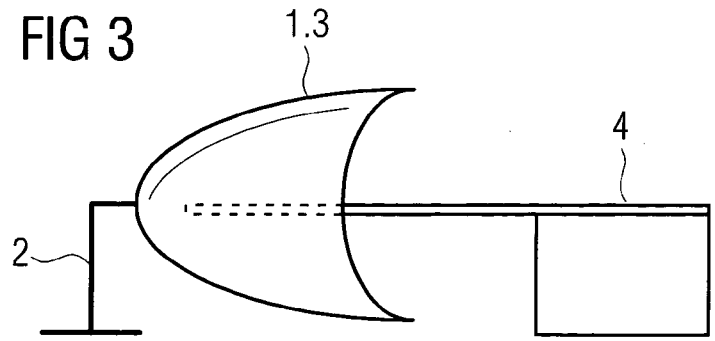
FIG. 3 a side view of an inventive collision protection device having a protective element in the form of an elliptical paraboloid surface in a shielding position relative to a patient examination table.

FIG. 3 shows a further inventive collision protection device having a protective element 1.3 in the form of an elliptical paraboloid surface, wherein the collision protection device also has a stand 2 and can be moved into the shielding position.

Figure 5:
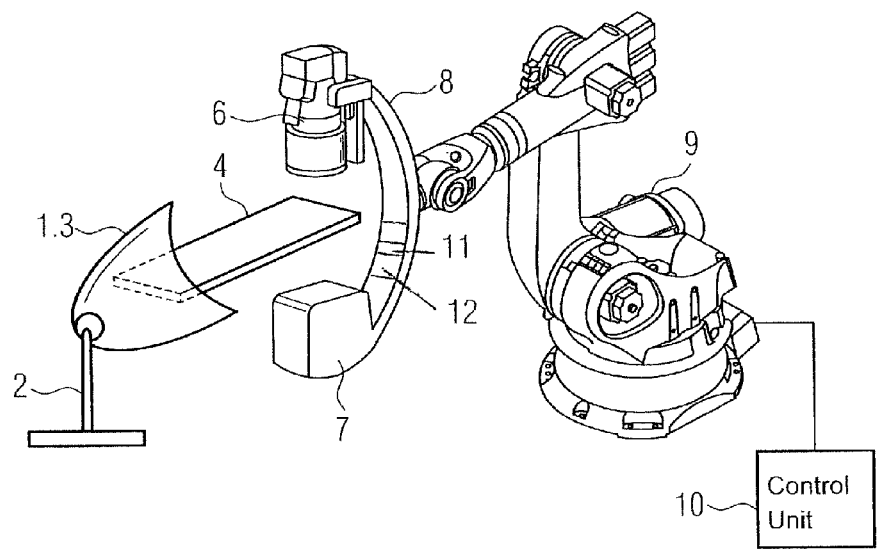
FIG. 5 an inventive X-ray device having a movable robotic arm, a patient examination table and a collision protection device.

The collision protection device is provided in particular as a mechanical shield for a patient in the case of an X-ray device having a movable robotic arm on which an X-ray emitter and/or an X-ray detector are/is mounted. According to FIG. 5, X-ray emitter 6 and X-ray detector 7 are fixed for example to a C-arm 8 and the latter is carried by the movable robotic arm, in particular a 6-axis articulated-arm robot 9. The X-ray device is controlled by a control unit 10 which, for example, can also control a possible movement of the patient examination table 4 and the protective element or elements.

The clinical workflow for using the collision protection device and the corresponding X-ray device with C-arm looks as follows, for example: 1. The protective element and the C-arm are located in their respective parking positions, 2. the protective element is brought from its parking position manually or automatically into the shielding position around the patient table, 3. the C-arm is driven manually or automatically into its starting position, 4. optionally, a test run of the C-arm (e.g. for a fast Dyna-CT run) is carried out in order to check the position of the C-arm relative to the position of the protective element, 5. image acquisition by means of the C-arm rotating around the patient table is started, 6. after the image acquisition or intervention has been completed the C-arm is first moved into its parking position, then the protective element is removed or also moved into its parking position.

The collision protection device is only brought into the shielding position at the patient table when there is a potential risk of a collision with the patient, e.g. when a fast rotation of a C-arm is necessary. In cases in which the rotational speed or path of the C-arm does not constitute a hazard, the collision protection device can be removed from the patient table, for example, or brought into a parking position. If necessary it can be moved back into the shielding position at any time.

The collision protection device or the protective element can be moved manually by the user, for example. Alternatively they can be moved in a motorized manner with the aid of a robot (also by means of the robotic arm of the C-arm, for example). Furthermore the automated movement of the collision protection device or protective element can be controlled from an external point, for example by means of a joystick from the control room of a catheter laboratory.

According to one embodiment of the invention the protective element is embodied as transparent. The protective element is advantageously embodied from plastic, in particular from a hard plastic which can withstand an impact with the C-arm for example. In order to minimize damage to the C-arm or X-ray detector in the event of a collision with the protective element, the protective element is coated on its outer surface with a flexible material, in particular a foam material. Alternatively the protective element is coated on the inside and/or outside with materials from nanotechnology which can be e.g. easily cleaned or sterilized. A decorative finish can also be applied to the inner and/or outer surface of the protective hood in order to create a pleasant ambience for the patient.

The protective element can be covered in a sterile manner, for example by means of a sterile sheath which is matched to the shape and size of the protective element. Alternatively it can be sterilized using methods well-known in the operating theater domain.

According to a further embodiment of the invention, a signaling device can be installed for example in the interior region of the protective element in order to facilitate communication between patient and medical staff. A loudspeaker or microphone system can be used, for example. Alternatively, holes for the purpose of an acoustic exchange can be present in the protective element.

In addition to the already mentioned advantages, the collision protection device according to the invention is easy to install, reasonable in terms of manufacturing and acquisition costs, and requires little maintenance and customer service.

Additional safety measures can also be installed: In order to avoid a collision between the patient table and the protective element, the protective element can be equipped with an integrated system of collision sensors comprising one or more sensors 11, in particular in the case of collision protection devices that are not directly coupled to the patient table. Since the patient table can be shifted back and forth or moved by the user during an examination, the collision sensor system ensures that a collision between the patient table and the protective element is avoided. For that purpose a signal output device 13, for example, can be provided which outputs an acoustic or optical warning signal. A movement of the patient table adjusted to the position of the protective element in the room can be possible. Said adjustment can take place once, a number of times or at regular intervals or be performed by the user in a similar manner to a calibration. For this, the user moves the patient table as far as its maximum position within the protective element in the shielding position and confirms this position (by pressing a button, for example); the new maximum position of the patient table is then stored within the protective element in the patient table's control system.

In order to avoid a collision between protective element and C-arm, the following procedure can be adopted for example: The shielding position of the protective element in the three-dimensional space is stored in a control system provided for controlling the C-arm. The movement paths of the C-arm are then calculated so that the C-arm travels around the protective element, i.e. such that the calculated path of the avoids the area of the protective element. The C-arm is equipped with a collision sensor system having at least one sensor 11.

The sensor system of the C-arm can be embodied for example in the form of feelers 12. Feelers of said kind are fixed to the surface of the C-arm and preferably consist of a soft material in which miniaturized sensors (e.g. capacitive contact sensors) are installed. Alternatively the feelers can consist of a hard material and be made movable by way of an adapted mechanism.

Alternatively the feelers consist of materials from nanotechnology development whose rigidity can be adjusted for example by means of suitable electrical impulses or which can generate light or fluorescence if the built-in sensors report a contact or collision with another object. If the C-arm comes into contact with an object or person, the sensors of the feelers affected report a signal. The assessment of the collision probability or of the extent of the contact can be calculated for example on the basis of the following information:

the intensity of the signal from the sensors;
the number of feelers or sensors that are affected and their surface;
the position of the contact on the housing of the C-arm and the distance from the point of contact to the housing;
how quickly adjacent sensors report a contact signal.

Alternatively or in addition, the sensor system can be integrated in the protective element, in the outside of the protective hood for example, and connected to the control system of the X-ray device. If there is a risk of a collision, the control system automatically alerts the user by means of a signal. Said signal can be optical or acoustic. For example, the outside of the protective hood that is affected by a possible collision lights up.

Alternatively or in addition to the methods already described, a video system can be used for support and collision avoidance purposes. For example, video images are acquired from different perspectives in the examination room; a reconstruction of the position of the C-arm and the collision protection device is performed in the 3-D space and in (quasi-)realtime. The movement paths of the C-arm and a collision probability are then calculated based on this information. From this, a signal is output to the user if there is a high risk of a collision.

In addition, at least one impact sensor can be positioned on the protective element, said sensor sending a signal to the control system of the X-ray device in order to stop the movement of the C-arm.

The invention can be summarized as follows: A collision protection device for a patient examination table of a medical X-ray device is provided for the purpose of assuring simple and reliable avoidance of collisions between very fast moving device parts of a medical X-ray device and a patient, which collision protection device has a protective element made of an X-ray transparent material, wherein the collision protection device can be arranged relative to the patient examination table and brought into a position such that in said position the protective element mechanically shields at least a part of the lying surface of the patient examination table.

The invention claimed is:

1. A collision protection device for a patient examination table of a medical X-ray device, comprising:
    a protective element made of an X-ray transparent material that mechanically shields at least a part of the patient examination table;
    a feeler;
    a collision sensor, wherein the collision sensor is arranged in the feeler; and
    a stand or a base directly connected to the collision protection device that decouples the collision protection device from the patient examination table.

2. The collision protection device as claimed in claim 1, wherein the protective element is transparent.

3. The collision protection device as claimed in claim 1, further comprising a securing element that couples the protective element to the patient examination table, wherein the securing element is a fixing post.

4. The collision protection device as claimed in claim 1, wherein the protective element is a longitudinally sectioned cylinder.

5. The collision protection device as claimed in claim 1, wherein the protective element is a cylinder.

6. The collision protection device as claimed in claim 1, wherein the protective element is an elliptical paraboloid, a half-ellipsoid, or a half-sphere.

7. The collision protection device as claimed in claim 1, wherein the protective element is made from plastic.

8. The collision protection device as claimed in claim 1, wherein the protective element is coated with a flexible material.

9. The collision protection device as claimed in claim 8, wherein the flexible material is a foam material.

10. The collision protection device as claimed in claim 1, further comprising a signal output device.

11. The collision protection device as claimed in claim 1, wherein the feeler is configured to generate a light or fluorescence signal if the sensor reports a contact or collision with another object.

12. An X-ray device, comprising:
a movable robotic arm;
an X-ray emitter arranged on the movable robotic arm;
an X-ray detector arranged on the movable robotic arm;
a patient examination table; and
a collision protection device comprising:
- a protective element made of an X-ray transparent material that mechanically shields at least a part of the patient examination table;
- a feeler;
- a collision sensor, wherein the collision sensor is arranged in the feeler; and
- a stand or a base directly connected to the collision protection device that decouples the collision protection device from the patient examination table.

13. The X-ray device as claimed in claim 12, wherein the robotic arm is a C-arm and the X-ray emitter and the X-ray detector are disposed at opposite ends of the C-arm.

14. The collision protection device as claimed in claim 13, wherein the feeler is fixed to the surface of the C-arm.

* * * * *